United States Patent [19]

Youngdale

[11] Patent Number: 5,075,434
[45] Date of Patent: Dec. 24, 1991

[54] ANTIDIABETIC 3-HALO-BETA-AMINOESTRANES

[75] Inventor: Gilbert A. Youngdale, Portage, Mich.

[73] Assignee: The Upjohn Company, Kalamazoo, Mich.

[21] Appl. No.: 576,425

[22] PCT Filed: Mar. 9, 1989

[86] PCT No.: PCT/US89/00892

§ 371 Date: Sep. 20, 1990

§ 102(e) Date: Sep. 20, 1990

Related U.S. Application Data

[63] Continuation of Ser. No. 175,811, Mar. 31, 1988, abandoned.

[51] Int. Cl.$^5$ .................. C07J 33/00; C07J 41/00; C07J 43/00
[52] U.S. Cl. .................. 540/106; 540/112; 540/117; 552/522
[58] Field of Search .............. 552/522; 540/112, 108, 540/117

[56] References Cited

FOREIGN PATENT DOCUMENTS

PCT/US86/-
02116 10/1986 PCT Int'l Appl. .

*Primary Examiner*—Mukund J. Shah
*Assistant Examiner*—E. C. Ward
*Attorney, Agent, or Firm*—Paul J. Koivuniemi; Debbie K. Wright

[57] ABSTRACT

This invention is a compound of formula 1 and pharmaceutically acceptable salts thereof;

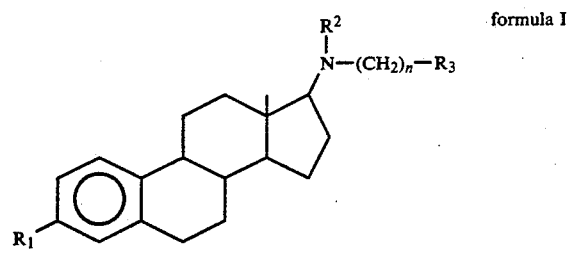

formula I wherein $R_1$ is fluorine, chlorine or bromine; wherein $R_2$ is hydrogen or $(C_1-C_3)$ alkyl; wherein n is one or 2; wherein $R_3$ is phenyl, 2-furyl, 3-furyl, 2-thienyl, 3-thienyl, 2-pyridinyl, 3-pyridinyl, 4-pyridinyl; wherein phenyl is optionally substituted with one substituent selected from the group consisting of halogen, trifluoromethyl or sulfonamide. These compounds are useful as hypoglycemic agents.

4 Claims, No Drawings

ANTIDIABETIC 3-HALO-β-AMINOESTRANES

CROSS REFERENCE TO RELATED APPLICATIONS

The present application is the national phase of PCT Application No. PCT/US89/00892, filed Mar. 9, 1989, which is a continuation of patent application Ser. No. 07/175811, filed Mar. 31, 1988, now abandoned.

FIELD OF INVENTION

This invention encompasses novel halogenated estranes substituted with an aminoalkyl sidechain that are useful for treating hyperglycemia associated diseases such as diabetes and obesity.

BACKGROUND

Hyperglycemia refers to a condition commonly found in patients suffering from mature-onset diabetes mellitus or other diseases which cause impairment of pancreatic function. Hyperglycemic patients with non-insulin dependent diabetes mellitus (NIDDM) with insulin resistance exhibit elevated serum glucose levels. Failure to adequately control elevated serum glucose levels can cause myocardioischemia, stroke, peripheral vascular disease, lethargy, coma, blindness, kidney failure or death. While conventional treatment for hyperglycemic conditions may include restriction of carbohydrate intake and insulin injection, one important means of treating hyperglycemic patients is with oral hypoglycemic agents. Hypoglycemic agents which would be particularly useful to treat hyperglycemia would be highly effective and exhibit no detrimental long term side effects.

INFORMATION DISCLOSURE

Steroidal compounds useful as hypoglycemic agents are described in the International Application PCT/US86/02116 which has an International Publication Date of Apr. 23, 1987.

SUMMARY OF THE INVENTION

This invention is a compound of formula 1 and pharmaceutically acceptable salts thereof; wherein $R_1$ is fluorine, chlorine or bromine; wherein $R_2$ is hydrogen or $(C_1-C_3)$ alkyl; wherein n is one or 2; wherein $R_3$ is phenyl, 2-furyl, 3-furyl, 2-thienyl, 3-thienyl, 2-pyridinyl, 3-pyridinyl, 4-pyridinyl; wherein phenyl is optionally substituted with one substituent selected from the group consisting of halogen, trifluoromethyl or sulfonamide. Compounds represented by formula I are useful as hypoglycemic agents in treating patients suffering from elevated serum glucose levels resulting from an impairment of tissue response to insulin and/or an impairment of pancreatic islet function such as non-insulin dependent diabetes mellitus (NIDDM) with insulin resistance.

DETAILED DESCRIPTION

The compounds of this invention are identified in two ways: by common name and by numerical identification which corresponds to the appropriate structure contained in the structure charts. In appropriate situations, the proper stereochemistry is represented in the structure charts as well.

The term alkyl means an aliphatic hydrocarbon radical and includes branched or unbranched forms such as methyl, ethyl, n-propyl, or isopropyl. In this document the parenthetical term $(C_n-C_m)$ is inclusive such that a compound of $(C_1-C_3)$ would include compounds with 1, 2, or 3 carbon atoms and their isomeric forms.

It will be apparent to those skilled in the art that compounds of this invention may contain chiral centers. The scope of this invention includes all enantiomeric or diastereomeric forms of formula I compounds either in pure form or as mixtures of enantiomers or diastereomers.

Both organic and inorganic acids can be employed to form non-toxic pharmaceutically acceptable salts of the compounds of this invention. Illustrative acids are sulfuric, nitric, phosphoric, hydrochloric, citric, acetic, lactic, tartaric, palmoic, ethanedisulfonic, sulfamic, succinic, cyclohexylsulfamic, fumaric, maleic, and benzoic acid. These salts are readily prepared by methods known in the art.

The compounds of this invention are prepared by the general scheme shown in Chart 1. The compounds of this invention are prepared from the halogenated estranone, C-1, by reacting the estranone with a commercially available or known amine of the formula H—N(—R$_2$)(—(CH$_2$)$_n$—R$_3$); when $R_2$ is hydrogen or $(C_1-C_3)$ alkyl, n is one or 2 and $R_3$ is a furyl, thienyl, pyridinyl or optionally substituted phenyl moiety, in the presence of sodium cyanoborohydride in a suitable solvent. The halogenated estranone, C-1; when $R_1$ is fluorine, chlorine or bromine, is prepared from the commercially available hydroxyestranone, C-3, which is converted to the aminoestranone, C-2, by methods well known in the art. A preferred process is described in Feiser and Feiser, Reagents in Organic Synthesis, Volume 4, 86-87. The aminoestranone, C-2, is converted to the halogenated erstranone by replacing the amino group with a halogen using the well known Sandmeyer Reaction.

Compounds of this invention represented by formula I are useful to treat NIDDM and its complications in mammals, including human beings because these compounds lower serum glucose levels when administered to KKA$^y$ mice with spontaneous diabetes. Accordingly, a patient to be treated with certain of the novel hypoglycemic compounds of this invention is first diagnosed as a diabetic by conventional means, usually by the persistence of elevated serum glucose levels, and a treatment regimen with compounds of this invention is established so that the elevation in a patient's serum glucose level is either significantly reduced or eliminated. The precise therapeutic endpoint of treatment, elimination or merely reduction in hyperglycemia, is readily determined by the attending physician based upon the clinical presentation and concomitantly employed treatment. For example, certain of the novel hypoglycemic compounds of this invention may be employed to significantly reduced hyperglycemia in a patient, with a carbohydrate restricted diet providing a further measure of control. Preferred patients to be treated are domesticated animals and humans, the most preferred patients are humans.

While the novel hypoglycemic compounds of this aspect of the invention may be administered by any convenient route; orally, subcutaneously, intravenously, intramuscularly, topically, or rectally, these compounds are most significantly and usefully employed as oral hypoglycemic agents, particularly in solid dosage form such as capsules and tablets. Alternatively, liquid oral dosage forms, such as syrups and elixirs, may be used. The oral pharmaceutical compositions in accordance with the present invention are all prepared by methods known in the art for preparing other oral antidiabetic compositions. Since an individual patient response to treatment with compounds in accordance with the present invention may vary, effective dosages of the compounds of the instant invention will vary from patient to patient. Ordinarily, an oral dosage of from 0.1 to 10 mg/kg of these compounds will be adequate to significantly reduce hyperglycemia in a patient being treated. Repeated dosages, every 4–12 hr, may be required during the day to maintain the antihyperglycemic effect. Accordingly, dosages from about 0.1 mg/kg/dose to about 10 mg/kg/dose, depending upon the patient, the frequency of treatment, and the observed response are preferred. An attending physician may initially prescribe a relatively small amount of a novel hypoglycemic compound of this invention and later increase this dosage as necessary to achieve the desired level of control.

Novel hypoglycemic compounds of the present invention are also useful to treat and/or prevent obesity in mammals including human beings. For this purpose, the novel compounds of this invention are formulated and administered as described above.

All compounds of the present invention may be formulated into pharmaceutical compositions, employing a pharmaceutically acceptable carrier. Pharmaceutical formulations include pharmaceutical compositions suitable for oral, parenteral, vaginal, topical, and rectal use, such as tablets, powder packets, cachets, dragees, suppositories, or bougies. Suitable diluents or carriers such as carbohydrates, proteins, lipids, calcium phosphate, cornstarch, stearic acid, or methylcellulose may be used as carriers or for coating purposes. Coconut oil, sesame oil, safflower oil, cottonseed oil, or peanut oil may be used for preparing solutions or suspensions and sweetening, coloring and flavoring agents may be added.

The utility of the compounds of this invention is shown in laboratory tests which determine serum glucose levels in mice. The results of these tests for a typical compound of this invention, 3-chloro-17$\beta$-[N-(3-trifluoromethylphenylmethyl)amino]estra-1,3,5(10)-triene, are given in Table 1. At the doses levels needed to find hypoglycemic effects, the compounds of this invention shows little or no estrogenic effects. The absence of significant estrogenic effects makes the compounds of this invention particularly effective in the long term clinical treatment of hyperglycemia.

TESTING FOR BLOOD GLUCOSE LOWERING IN THE KKA$^y$ MOUSE

All KKA$^y$ mice used for screening are produced and selected by methods previously outlined, T. Fujita et al., Diabetes, 32, 804–10 (1983). The screening is done in groups of six animals per group.

Pre-treatment nonfasting blood glucose (NFBG) samples are measured 5 days prior to the start of a screening run by previously described methodologies. These blood sugar values are used to place animals into groups with equal mean blood glucose concentrations and to eliminate any mice with a NFBG value <250 mg/dl. On day 0, compounds chosen to be run are incorporated into ground mouse chow (Purina 5015). Compounds are included at a rate of 1 mg/gram of chow. Generally, 300 g of drugs containing diet is prepared for each group. Mice receiving ground chow only are the negative control. Each screening run also uses ciglitazone (T. Fujita, et al., supra) as a positive control (0.5 to 1.0 mg/gram chow).

Initial body and food weights are taken on day 1. Food is placed in a crock which contains an adequate amount to last for the length of the study. In order to acclimate the mice from pelleted mouse chow to ground mouse chow, they are fed the ground chow for 9 days prior to use in the screen. On day 4 of treatment, a NFBG sample is again measured, as well as food and body weights. Food consumption measurements are used to determine an average mg/kg dose the mice received over the testing period, and to evaluate the compound's effect on food consumption.

Acceptance and activity are determined by the following criteria:

A. Negative Control

This group must not show a significant change ($p<0.05$) from pre- to post-treatment. If there is a significant decrease in blood sugar the run is not valid.

B. Positive Control

This group must show a significant depression in blood sugar mean levels from pre- to post-treatment. A lack of activity in this group would also invalidate the run.

C. Negative Control vs. Positive Control

This contrast must be significant. It is a further assurance that both control groups performed as expected.

D. Compound

A compound's activity is based on several criteria:
(1) A significant decrease in blood sugar mean levels from pre- to post-treatment.
(2) Negative control vs. compound: This contrast allows one to determine if these groups are dissimilar, which is required for the compound to be considered active.

Without further elaboration, it is believed that one skilled in the art can, using the preceding description, practice the present invention to its fullest extent. The following detailed examples describe how to prepare various compounds of the invention and are to be construed as merely illustrative, and not limitations of the preceding disclosure. Those skilled in the art will promptly recognize appropriate variations from the procedures both as to reactants and as to reaction conditions and techniques.

EXAMPLES

Example 1

3-Chloroestra-1,3,5(10)-trien-17-one

A solution of sodium nitrite (0.95 g) in water (60 ml) is slowly added to a solution cooled in an ice-salt bath of 3-aminoestra-1,3,4(10)-trien-17-one (3.22 g) in 2N hydrochloric acid (150 ml). The mixture is stirred for 1.5 hours, ethanol (150 ml) is added and the mixture is stirred an additional 1 hour. Cupric chloride (6 g) in 6N hydrochloric acid is added, the mixture is stirred for 1 hour, allowed to warm to ambient temperatures and stirred for 18 hours. The mixture is diluted with water (200 ml), filtered, chromatographed on silica gel, and recrystillized in methylene chloride/hexane to give the title compound (1.61 g).

Calc. for $C_{18}H_{21}ClO$: C, 74.85; H, 7.33; Cl, 12.28.
Found: C, 75.14; H, 7.36; Cl, 12.21.

Example 2

3-Chloro-17β-[N-(3-trifluoromethylphenylmethyl)-amino]estra-1,3,5(10)-triene

The compound, 3-chloroestra-1,3,5(10)-trien-17-one (2.17 g) is added to a solution of 3-(trifluoromethyl)benzylamine (2.6 g) in methanol (200 ml) and tetrahydrofuran (200 ml) made acidic with acetic acid (1.5 ml). When the starting material is dissolved, sodium cyanoborohydride (0.72 g) is added, the mixture is stirred 24 hours, additional sodium cyanoborohydride (0.7 g) is and the mixture is stirred for another 21 hours. The mixture is diluted with water (200 ml), made basic with 50% sodium hydroxide and extracted with methylene chloride (3×100 ml). The combined extracts are washed with brine, dried over magnesium sulfate and the solvent is removed. The product is chromatographed on silica gel and recrystallized in methylene chloride/hexane to give the title compound (2.26 g).

Melting point: 97°–101° C.

FORMULAS

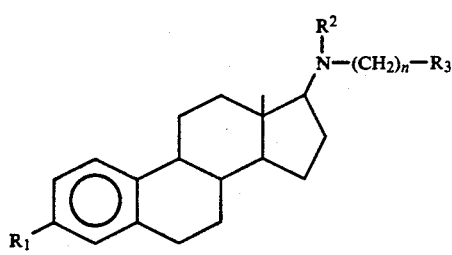

formula I

TABLE 1

| | Results of Compound 3-Chloro-17β-[N-(3-trifluoro-methylphenylmethyl)-amino]estra-1,3,5(10)-triene | | | | | | | |
|---|---|---|---|---|---|---|---|---|
| | MISS | | Nonfasting Blood Glucose | | Body Weight | | Food Difference Day 1–Day 4 | |
| Test Stage | NFBG T/C | Index | Cmpd Pre | Cmpd Post | Cmpd Pre | Cmpd Post | Cmpd | Control |
| 1 | 0.52 | 1.351 | 331 | 144 | 47.5 | 47.3 | 16.1 | 21.3 |

CHART 1

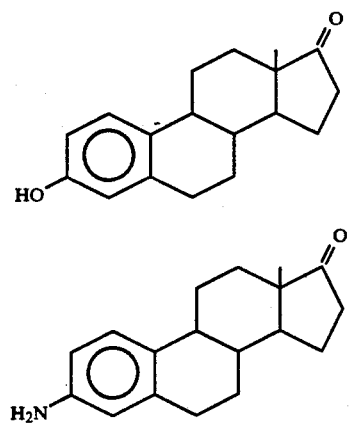

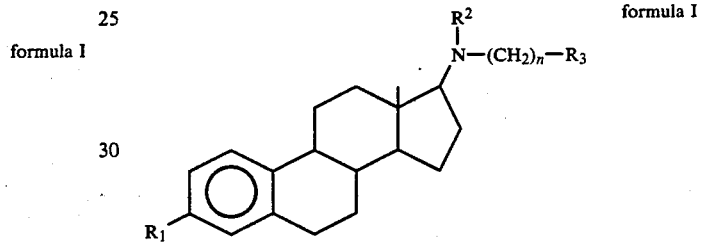

I claim:
1. A compound of formula 1 and pharmaceutically acceptable salts thereof;

wherein $R_1$ is fluorine, chlorine or bromine;
wherein $R_2$ is hydrogen or ($C_1$–$C_3$) alkyl;
wherein n is one or 2;
wherein $R_3$ is phenyl, 2-furyl, 3-furyl, 2-thienyl, 3-thienyl, 2-pyridinyl, 3-pyridinyl, 4-pyridinyl;
wherein phenyl is optionally substituted with one substituent selected from the group consisting of halogen, trifluoromethyl or sulfonamide.

2. A compound according to claim 1 wherein $R_2$ is hydrogen, wherein n is one; and wherein $R_3$ is phenyl substituted with one substituent selected from the group consisting of halogen, trifluoromethyl, or sulfonamide.

3. A compound according to claim 1 wherein $R_2$ is hydrogen, wherein n is one; and wherein $R_3$ 2-furyl, 3-furyl, 2-thienyl, 3-thienyl, 2-pyridinyl, 3-pyridinyl, or 4-pyridinyl.

4. A compound according to claim 2 which is 3-fluoro-17β-[(N-(3-trifluoromethyl)phenylmethyl)amino]-estra-1,3,5(10)-triene; 3-chloro-17β-[(N-(3-trifluoromethyl)phenylmethyl)amino]-estra-1,3,5-(10)-triene; or 3-bromo-17β-[(N-(3-trifluoromethyl)phenylmethyl)-amino]-estra-1,3,5-(10)-triene;

* * * * *